US006768005B2

(12) United States Patent
Mellor et al.

(10) Patent No.: US 6,768,005 B2
(45) Date of Patent: Jul. 27, 2004

(54) PROCESS

(75) Inventors: Ben James Mellor, Grangemouth (GB); Donald Alfred Wellings, Northwich (GB); Mark Edward Douglas, Manchester (GB)

(73) Assignee: Avecia Limited, Manchester (GB)

( * ) Notice: Subject to any disclaimer, the term of this patent is extended or adjusted under 35 U.S.C. 154(b) by 0 days.

(21) Appl. No.: 09/740,031

(22) Filed: Dec. 20, 2000

(65) Prior Publication Data

US 2002/0111479 A1 Aug. 15, 2002

(51) Int. Cl.[7] ........................ C07H 21/00; C07H 21/04; C12P 19/34

(52) U.S. Cl. .................. 536/25.3; 536/23.1; 536/25.34; 435/91.1

(58) Field of Search ............................... 536/23.1, 25.3, 536/25.34; 435/91.1, 72, 6

(56) References Cited

U.S. PATENT DOCUMENTS

| | | | | |
|---|---|---|---|---|
| 4,753,985 A | | 6/1988 | Rosevear et al. | |
| 4,795,700 A | | 1/1989 | Dervan et al. | |
| 5,047,524 A | * | 9/1991 | Andrus et al. | 536/25.31 |
| 5,164,491 A | | 11/1992 | Froehler et al. | |
| 5,362,866 A | | 11/1994 | Arnold, Jr. | |
| 5,407,795 A | | 4/1995 | Kolberg et al. | |
| 5,514,789 A | | 5/1996 | Kempe | |
| 5,981,734 A | * | 11/1999 | Mirzabekov et al. | 536/25.3 |
| 6,096,881 A | * | 8/2000 | Han et al. | 536/25.3 |
| 6,111,086 A | | 8/2000 | Scaringe | |
| 6,300,486 B1 | | 10/2001 | Froehler et al. | |

FOREIGN PATENT DOCUMENTS

| | | |
|---|---|---|
| EP | 0288310 A2 | 10/1988 |
| EP | 0323152 A2 | 7/1989 |
| EP | 1028124 A2 | 8/2000 |
| WO | WO92/09615 | 6/1992 |
| WO | WO94/01446 | 1/1994 |
| WO | WO97/40458 | 10/1997 |
| WO | WO00/20431 | 4/2000 |
| WO | WO 00/46231 | 8/2000 |
| WO | WO01/96358 | 12/2001 |

OTHER PUBLICATIONS

Arshady et al., "Easily Prepared Polar Support for Solid Phase Peptide and Oligonucleotide Synthesis. Preparation of Substance P and a Nonadeoxyribonucleotide" *J.C.S. Chem. Comm.* (1979) 423–425.

Montserrat et al., "Criteria for the Economic Large Scale Solid–Phase Synthesis of Oligonucleotides" *Tetrahedron* 50:8 (1994) pp. 2617–2622.

Bardella et al., "Polysytyrene–Supported Synthesis by the Phosphite Triester Approach: An Alternative for the Large–Scale Syntheisis of Small Oliodeoxyribonucleotides" *Tetrahedron Letters* 31:43 (1990) pp. 6231–6234.

Gait et al., "Synthesis of Oligodeoxyribonucleotides by a Continuous–flow, Solid–phase Method Using Phosphotriester Intermediates" *J. Chem Soc., Chem Commun.* (1982) pp. 37–40.

* cited by examiner

*Primary Examiner*—Sean McGarry
*Assistant Examiner*—Janet L. Epps-Ford
(74) *Attorney, Agent, or Firm*—Pillsbury Winthorp LLP

(57) ABSTRACT

A process for the synthesis of phosphorothioate oligonucleotides is provided which comprises assembling an oligonucleotide bound to a solid support in the presence of acetonitrile; prior to cleaving the oligonucleotide from the solid support removing the acetonitrile; and cleaving the oligonucleotide from the solid support. The process is particularly suited to the large scale synthesis of nucleotides.

10 Claims, No Drawings

PROCESS

The present invention concerns a method for the synthesis of phosphorothioate triesters, and particularly oligonucleotides.

In the past 15 years or so, enormous progress has been made in the development of the synthesis of oligodeoxyribonucleotides (DNA sequences), oligoribonucleotides (RNA sequences) and their analogues 'Methods in Molecular Biology, Vol. 20, Protocol for Oligonucleotides and Analogs', Agrawal, S. Ed., Humana Press, Totowa, 1993. Much of the work has been carried out on a micromolar or even smaller scale, and automated solid phase synthesis involving monomeric phosphoramidite building blocks Beaucage, S. L.; Caruthers, M. H. *Tetrahedron Lett.*, 1981, 22, 1859–1862 has proved to be the most convenient approach. Indeed, high molecular weight DNA and relatively high molecular weight RNA sequences can now be prepared routinely with commercially available synthesisers. These synthetic oligonucleotides have met a number of crucial needs in biology and biotechnology.

Whereas milligram quantities have generally sufficed for molecular biological purposes, gram to greater than 100 gram quantities are required for clinical trials. Several oligonucleotide analogues that are potential antisense drugs are now in advanced clinical trials. If, as seems likely in the very near future, one of these sequences becomes approved, say, for the treatment of AIDS or a form of cancer, kilogram, multikilogram or even larger quantities of a specific sequence or sequences will be required.

Many of the oligonucleotides currently of interest in the phamaceutical industry are analogues of natural oligonucleotides which comprise phosphorothioated-internucleoside linkages. When phosphorothioate linkages are present, particularly when such linkages comprise a major proportion of the linkages, and especially when they comprise 100% of the internucleoside linkages, it is highly desirable that the concentration of impurity, non-phosphorothioated linkages in the final product is kept to a pharmacologically acceptable level.

A large number of protocols for the synthesis of oligonucleotides employ acetonitrile as a solvent for the reagents employed. Acetonitrile is attractive as a solvent because it is inert towards the reagents and oligonucleotide product, it has good solvation properties and is environmentally acceptable. Commonly, for large-scale syntheses, a high concentration of acetonitrile is present during the stage when the oligonucleotide product is cleaved from the solid support. Hitherto, this has been acceptable for large scale synthesis because of the perceived inert nature of acetonitrile. However, during the course of the studies resulting in the present invention, it has now been surprisingly found that higher purity oligonucleotides can be obtained by reducing the concentration of acetonitrile present during the cleavage stage.

According to one aspect of the present invention, there is provided a process for the large-scale synthesis of phosphorothioate oligonucleotides which comprises:

a) assembling an oligonucleotide bound to a solid support in the presence of acetonitrile; and b) cleaving the oligonucleotide from the solid support;

characterised in that the concentration of acetonitrile is reduced to less than 10% by weight of the oligonucleotide plus solid support prior to the cleavage of the oligonucleotide from the solid support.

The phosphorothioate oligonucleotides can be assembled by known techniques for solid phase synthesis, for example using H-phosphonate or particularly phosphoramidite chemistry. For the phosphoramidite approach, commonly, the sequence employed is: deprotection of the nucleoside bound to solid support, preferably at the 5'-position; coupling of a, preferably 3'-, phosphoramidite nucleoside to form a supported oligonucleotide; sulphurisation of the supported oligonucleotide by reaction with a sulphurising agent to produce a supported phosphorothioate oligonucleotide; and capping of unreacted supported nucleoside with a capping reagent. This cycle is then repeated as often as is necessary to assemble the desired sequence of the oligonucleotide. When a mixed phosphate/phosphorothioate product is desired, the sulphurisation stage can be replaced with an oxidation step to produce a phosphate linkage at the desired location. On completion of the assembly, and prior to cleavage from the support, the supported oligonucleotide is commonly washed with acetonitrile in order to remove traces of unreacted reagents.

Acetonitrile can be removed by drying of the supported oligoncleotide, optionally under reduced pressure. The acetonitrile is commonly removed at ambient temperature, for example from 15 to 30° C., although elevated temperatures, such as from 30 to 80° C., for example from 40 to 60° C., may be employed.

The process according to the first aspect of the present invention is employed for large scale synthesis of oligonucleotides. Large scale synthesis of oligonucleotides is often regarded as being at or above a batch size of 10 mmol oligonucleotide, commonly at or above 15 mmol, often at or above 25 mmol, for example greater than 50 mmol, and especially greater than 75 mmol of oligonucleotide. In many embodiments, the process of the present invention is employed for oligonucleotide synthesis at a scale in the range of from 100–500 mmol.

On completion of the assembly of the desired product, the product may be cleaved from the solid support. Cleavage methods employed are those known in the art for the given solid support. When the product is bound to the solid support via a cleavable linker, cleavage methods appropriate for the linker are employed, for example, contact with methylamine, aqueous methylamine solution, liquified ammonia, gaseous ammonia and particularly contact with concentrated aqueous ammonia solution. Following cleavage, the product can be purified using techniques known in the art, such as one or more of ion-exchange chromatography, reverse phase chromatography, and precipitation from an appropriate solvent. Further processing of the product by for example ultrafiltration may also be employed.

Solid supports that are employed in the process according to the present invention are substantially insoluble in the solvent employed, and include those supports well known in the art for the solid phase synthesis of oligonucleotides. Examples include silica, controlled pore glass, polystyrene, copolymers comprising polystyrene such as polystyrene-poly(ethylene glycol) copolymers and polymers such as polyvinylacetate. Additionally, microporous or soft gel supports, especially poly(acrylamide) supports, such as those more commonly employed for the solid phase synthesis of peptides may be employed if desired. Preferred poly(acrylamide) supports are amine-functionalised supports, especially those derived from supports prepared by copolymerisation of acryloyl-sarcosine methyl ester, N,N-dimethylacrylamide and bis-acryloylethylenediamine, such as the commercially available (Polymer Laboratories) support sold under the catalogue name PL-DMA. The procedure for preparation of the supports has been described by Atherton, E.; Sheppard, R. C.; in *Solid Phase Synthesis: A Practical Approach*, Publ., IRL Press at Oxford University Press (1984). The functional group on such supports is a methyl ester and this is initially converted to a primary amine functionality by reaction with an alkyl diamine, such as ethylene diamine.

According to a second aspect of the present invention, there is provided a process for the synthesis of phosphorothioate oligonucleotides which comprises:

a) assembling an oligonucleotide bound to a solid support in the presence of acetonitrile;

b) prior to cleaving the oligonucleotide from the solid support washing the oligonucleotide bound to a solid support with a solvent other than acetonitrile; and c) cleaving the oligonucleotide from the solid support.

Solvents which can be employed are preferably inert solvents which do not degrade the oligonucleotide under the conditions under which the solvent is employed. Examples of inert solvents that can be employed include inert organic solvents and inert aqueous solvents.

Preferably, the washing with solvent is effected such that the concentration of acetonitrile is reduced to less than 10% by weight of the oligonucleotide plus solid support.

Organic solvents which can be employed include aromatic hydrocarbons, for example toluene; aliphatic hydrocarbons, for example cyclohexane; haloalkanes, particularly dichloromethane; esters, particularly alkyl esters such as ethyl acetate and methyl or ethyl propionate; alcohols, particularly aliphatic alcohols such as $C_{1-4}$ alkyl alcohols, for example methanol, ethanol or isopropanol; amides, such as dimethylformamide and N-methylpyrollidinone; basic, nucleophilic solvents such as pyridine or alkylamines, especially tri(alkyl), such as tri($C_{1-4}$-alkyl) amines; ethers such as tetrahydrofuran; and sulphoxides, for example dimethylsulphoxide. Preferred solvents are tri (alkyl)amines, most preferably triethylamine.

Aqueous solvents that can be employed include water, aqueous buffer solutions, mixtures of water and water miscible inert organic solvents, especially those solvents described above.

Solid supports that may be employed are those described with the respect to the first aspect of the present invention. In many embodiments, it may be preferred to employ an organic solvent when the support is; hydrophobic, such as poly(styrene). In other embodiments, it may be preferred to employ an aqueous solvent when the support is hydrophilic, such as controlled pore glass or silica. In further embodiments, when the support is microporous, it may be preferred to employ a solvent which swells the support.

The process according to the second aspect of the present invention can be employed in both small (ie <25 mmol scale) and large scale oligonucleotide synthesis as described above in respect of the first aspect of the present invention.

The oligonucleotides can be assembled, and cleaved from the solid support, by the methods described above in respect of the first aspect of the present invention.

In both the first and second aspects of the present invention, the acetonitrile concentration is preferably reduced to less than 5%, often less than 3%, particularly less than about 2%, and especially less than about 1%, by weight of the oligonucleotide plus solid support.

The synthesis of oligonucleotides using phosphoramidite chemistry wherein the oligonucleotide is synthesised supported on a microporous support is believed to be novel. Accordingly, in a third aspect of the present invention, there is provided a process for the preparation of an oligonucleotide which comprises coupling a nucleoside or oligonucleotide phosphoramidite with a nucleoside or oligonucleotide comprising a free hydroxy group supported on a solid support to form an oligonucleotide phosphite triester, characterised in that the solid support is a microporous support.

Microporous supports are preferably poly(acrylamide) supports, such as those more commonly employed for the solid phase synthesis of peptides, may be employed if desired. Preferred poly(acrylamide) supports are amine-functionalised supports, especially those derived from supports prepared by copolymerisation of acryloylsarcosine methyl ester, N,N-dimethylacrylamide and bis-acryloylethylenediamine, such as the commercially available (Polymer Laboratories) support sold under the catalogue name PL-DMA. The procedure for preparation of the supports has been described by Atherton, E.; Sheppard, R. C.; in *Solid Phase Synthesis: A Practical Approach*, Publ., IRL Press at Oxford University Press (1984), the microporous supports of which are incorporated herein by reference. The functional group on amine-functionalised supports is a methyl ester and this is initially converted to a primary amine functionality by reaction with an alkyl diamine, such as ethylene diamine.

The process according to the third aspect of the present invention is preferably carried out in the presence of a solvent which swells the microporous support. Examples of such solvents include haloalkanes, particularly dichloromethane; esters, particularly alkyl esters such as ethyl acetate and methyl or ethyl propionate; ethers such as tetrahydrofuran; and preferably amides, such as dimethylformamide and N-methylpyrollidinone. The most preferred solvent is dimethylformamide.

The nucleoside or oligonucleotide phosphoramidite employed can comprise a 3'- or 5'-phosphoramidite group, most preferably a 3'-phosphoramidite group. The nucleoside or oligonucleotide phosphoramidite commonly comprises a protected hydroxy group at whichever of the 3'- or 5'-positions is not a phosphoramidite. Preferably, at the 5'-position is a protected hydroxy group. Preferred protecting groups are pixyl and trityl, especially dimethoxytrityl, groups.

The nucleoside or oligonucleotide comprising a free hydroxy group employed can comprise a 3'- or 5'-hydroxy group, and is commonly bound to the solid support via whichever of the 3'- or 5' positions is not free hydroxy. Most preferably, the nucleoside or oligonucleotide comprising a free hydroxy group is bound to the solid support via the 3'-position, and comprises a free 5' hydroxy group.

The nucleoside or oligonucleotide comprising a free hydroxy group is commonly bound to the solid support via a cleavable linker.

The coupling of the nucleoside or oligonucleotide phosphoramidite with a nucleoside or oligonucleotide comprising a free hydroxy group takes place in the presence of a suitable activator. Examples of such activators are those known in the art for conventional phosphoramidite oligonucleotide synthesis, and include tetrazole, thioethyltetrazole, nitrophenyltetrazole and dicyanoimidazole. Commonly, the nucleoside or oligonucleotide phosphoramidite is employed as a solution in the solvent employed to swell the microporous support. Advantageously, the phosphoramidite solution is mixed with the swollen support comprising the free hydroxy group prior to addition of the activator as a solution in the solvent employed to swell the microporous support.

The oligonucleotide phosphite triester produced in the process of the third aspect of the present invention is commonly oxidised or sulphurised to form an oligonucleotide phosphate or phosphorothioate. Oxidising agents employed are those known in the art for conventional phosphoramidite oligonucleotide synthesis, and include iodine and t-butylhydroperoxide. Sulphurising agents employed are those known in the art for conventional phosphoramidite oligonucleotide synthesis, and include xanthane hydride, phenylacetyl disulphide and Beaucage reagent. The oxidising or sulphurising agents are commonly employed as a solution in the solvent employed to swell the microporous support.

A capping treatment, employing capping agents known in the art, for example a mixture of pyridine and acetic anhydride and a mixture of pyridine and N-methylimidazole, may be employed. Advantageously, the capping agents are employed in the presence of the solvent employed to swell the microporous support.

Pixyl or trityl protecting groups present in the oligonucleotide phosphate or phosphorothioate bound to the solid support, commonly at the 5'-position, can be removed by conventional detritylation techniques, for example by treatment with a solution of dichloroacetic acid. Preferably the dichloroacetic acid is employed as a solution in the solvent employed to swell the microporous support, for example dichloromethane or advantageously and amide, particularly dimethylformamide or N-methylpyrrolidinone. Removal of the pixyl or trityl protecting groups produces a free hydroxyl group which can then be employed for further coupling. Further couplings can be carried out in order to assemble the desired sequence. On completion of the assembly of the desired sequence, the product can be cleaved from the solid support using techniques appropriate to the linker employed.

The processes according to the present invention can be employed to synthesise phosphorothioated deoxyribonucleotides and ribonucleotides. The nucleotides may comprise bases, protecting groups and other modifications known in the nucleotide art. For example, bases which may be present include purines and pyrimidines, commonly A, G, T, C and U. Other bases which may be present include hypoxanthine, inosine and 2,6-diaminopurine. Protecting groups which may be present include base-protecting groups, such as benzyl, acetyl, phenoxyacetyl and isobutyryl groups, and hydroxy-protecting groups, such as pixyl and trityl, especially dimethoxytrityl, groups. Ribonucleotides may be modified at the 2'-position by an alkoxy or alkoxyalkyl substituent, such as a methoxy or methoxyethoxy substituent or may be protected at the 2'-position by a hydroxy protecting group such as tertiary butyldimethylsilyl, 1-(2-fluorophenyl)-4-methoxypiperidine-4-yl (Fpmp) or 1-(2-chlorophenyl)-4-methoxypiperidine-4-yl (Cpmp). Other modifications, including inverted nucleosides, abasic nucleosides and L-nucleosides may also be present. Deoxyribonucleotides may be modified at the 2'-position by a 2'-C-alkyl group. Chimeric nucleotides, including mixed deoxyribonucleotides and ribonucleotides, and/or mixed phosphate/phosphorothioate nucleotides can be prepared.

In many embodiments, the processes of the present invention are employed to prepare oligonucleotides having from 1 to 100, often from 5 to 75, preferably from 8 to 50 and particularly preferably from 10 to 30 internucleoside linkages. Commonly, the process of the present invention are employed to prepare compounds wherein at least 50% of the internucleoside linkages are phosphorothioated, preferably at least 75%, and most preferably 90 to 100% phosphorothioated.

Examples of cleavable linkers that may be employed in the processes of the present invention include those well known in the art for the solid phase synthesis of oligonucleotides, such as urethane, oxalyl, succinyl, and amino-derived linkers. Succinyl linkers are preferred.

The invention will now be illustrated without limitation by the following examples.

EXAMPLES AND COMPARISON

A sample of a fully phosphorothioated deoxyribonucleotide comprising 17 phosphorothioate groups was prepared using standard phosphoramidite chemistry. The product was produced trityl-on on a polystyrene support. After completion of the assembly and sulphurisaton, the supported nucleotide was washed with acetonitrile.

Three samples of the supported oligonucleotide were treated as follows. For Example 1, the supported oligonucleotide was air dried on a filter funnel. For Example 2, the sample was washed with triethylamine. For Example 3, the sample was washed with 2.5 M aqueous sodium acetate solution. In each of Examples 2 and 3, the washing took place on a filter funnel under slightly reduced pressure, but operated so as to minimise evaporation of acetonitrile. The acetonitrile contents (% w/w) of the samples were measured by GC. The products of Examples 1 to 3 were cleaved using standard ammonolysis conditions using concentrated aqueous ammonia to obtain the oligonucleotide product. For Comparison A, a further sample of the supported was cleaved under the same conditions without a drying or washing treatment. In each case, the weight percentage of P=O impurity in the samples was determined using Ion exchange chromatography. The results are given in Table 1 below.

TABLE 1

| SAMPLE | Acetonitrile Content | % P = O |
|---|---|---|
| Comparison A | 33% | 9% |
| Example 1 | <1% | 5% |
| Example 2 | 1% | 5% |
| Example 3 | 9% | 5% |

The results given in Table 1 show that the oligonucleotide produced by the processes of the present invention (Examples 1 to 3) gave significantly purer oligonucleotide products than the comparative process wherein the concentration of acetonitrile was not reduced prior to cleavage.

What is claimed is:

1. A process for the preparation of an oligonucleotide which comprises coupling a nucleoside or oligonucleotide phosphoramidite with a nucleoside or oligonucleotide comprising a free hydroxy group supported on a solid support to form an oligonucleotide phosphite triester, wherein the solid support is a poly(acrylamide) microporous support.

2. A process according to claim 1, wherein the solid support is an amine-functionalized support derived from a polymer prepared by copolymerisation of acryloyl-sarcosine methyl ester, N,N-dimethylacrylamide and bis-acryloylethylenediamine.

3. A process according to claim 2, wherein the amine-functionalized support comprises a primary amine functionality derived from reaction of the methyl ester group with an alkyl diamine, preferably ethylene diamine.

4. A process according to claim 1, wherein the oligonucleotide is bound to the solid support via a cleavable linker selected from the group consisting of urethane, oxalyl, succinyl, and amino-derived linkers.

5. A process according to claim 1, which is employed to prepare oligonucleotides having from 1 to 100 internucleoside linkages.

6. A process according to claim 1, which is employed to prepare compounds wherein at least 50% of the internucleoside linkages are phosphorothioated.

7. A process according to claim 6, wherein 90 to 100% of the internucleoside linkages are phosphorothioated.

8. A process according to claim 3, wherein the alkyl diamine is ethylene diamine.

9. A process according to claim 1, wherein the oligonucleotide is cleaved from the solid support by contact with a cleaving reagent.

10. A process according to claim 9 wherein the cleavage reagent comprises methylamine, aqueous methylamine solution, liquefied ammonia, gaseous ammonia or concentrated aqueous ammonia solution.

* * * * *